United States Patent
Jordfald

(12) 
(10) Patent No.: US 6,585,641 B1
(45) Date of Patent: Jul. 1, 2003

(54) TRANSESOPHAGEAL PROBE WITH VARIABLE STIFFNESS

(75) Inventor: Dag Jordfald, Horteu (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 138 days.

(21) Appl. No.: 09/705,119

(22) Filed: Nov. 2, 2000

(51) Int. Cl.$^7$ .................................................. A61B 1/00
(52) U.S. Cl. ...................................... 600/144; 600/152
(58) Field of Search ............................ 600/144, 143, 600/439, 120, 459, 114, 152

(56) References Cited

U.S. PATENT DOCUMENTS

| | | | | |
|---|---|---|---|---|
| 4,893,613 A | * | 1/1990 | Hake | 600/152 |
| 4,930,521 A | | 6/1990 | Metzger et al. | 128/786 |
| 5,025,778 A | | 6/1991 | Silverstein et al. | 128/4 |
| 5,105,819 A | * | 4/1992 | Wollschainger | 600/463 |
| 5,156,155 A | * | 10/1992 | King | 600/463 |
| 5,390,661 A | * | 2/1995 | Griffith et al. | 600/114 |
| 5,398,689 A | * | 3/1995 | Connor et al. | 600/463 |
| 5,479,930 A | * | 1/1996 | Gruner et al. | 600/459 |
| 5,634,466 A | | 6/1997 | Gruner | 128/662.06 |
| 5,676,635 A | * | 10/1997 | Levin | 600/120 |
| 5,683,348 A | * | 11/1997 | Diener | 600/143 |
| 5,873,817 A | * | 2/1999 | Kokish et al. | 600/143 |
| 5,931,788 A | | 8/1999 | Keen et al. | 600/462 |
| 6,142,941 A | * | 11/2000 | Benhalima et al. | 600/439 |

FOREIGN PATENT DOCUMENTS

| | | | | |
|---|---|---|---|---|
| EP | 1017444 | | 7/2000 | |
| WO | WO 92/03963 | * | 3/1992 | A61B/1/00 |
| WO | WO 98/18519 | | 5/1998 | |
| WO | WO 00/33910 | | 5/2000 | |
| WO | WO 01/23022 | * | 4/2001 | A61M/5/178 |

OTHER PUBLICATIONS

European Search Report application No. 01309268.9–1265 dated Sep. 09, 2002.

* cited by examiner

Primary Examiner—Teresa Walberg
Assistant Examiner—Leonid M Fastovsky
(74) Attorney, Agent, or Firm—McAndrews, Held & Malloy, Ltd.; Peter J. Vogel; Michael A. Dellapenna

(57) ABSTRACT

A transesophageal probe with variable stiffness has a probe head connected to a distal end of an endoscope. A flexible tube is secured to the endoscope. Finally, a semi-rigid rod is slidably disposed within the flexible tube. Advancing or retracting the semi-rigid rod within the flexible tube allows the operator to vary the stiffness of the transesophageal probe.

18 Claims, 1 Drawing Sheet

(LOW)

(HIGH)

TRANSESOPHAGEAL PROBE WITH VARIABLE STIFFNESS

BACKGROUND OF THE INVENTION

This invention is directed to transesophageal echocardiography (TEE) probes used for imaging human organs, particularly the heart. TEE probes are well known in the art and comprise an ultrasonic transducer mounted at the end of a semi-flexible endoscope. The endoscope typically has an articulation section at its distal end that allows the operator to rotate or move the distal end of the endoscope such that the ultrasonic transducer is optimally positioned for imaging the relevant organ. Movement of the articulation section is effected in a controlled manner through mechanical controls (e.g., handles or knobs) positioned on a handle located on the proximal end of the endoscope.

In prior TEE probes, the semi-flexible nature of the endoscope enabled physicians or clinicians to introduce the ultrasonic transducer through the esophagus of a patient to a position where the heart or other relevant structure could be ultrasonically imaged. This was particularly useful during open-heart surgery, when conventional ultrasonic imaging was impractical due to the existence of an open chest cavity. In addition, TEE probes were useful when obesity or other anatomical anomalies precluded the use of conventional ultrasonic imaging. However, because of their uniform stiffness, introducing prior TEE probes into the esophagus was difficult and required significant clinical skill because of the variations in esophageal anatomy. Also, once introduced, there was no means for changing the stiffness characteristics of the TEE probe.

Therefore, there is a need for a TEE probe with variable stiffness characteristics that address these prior problems.

BRIEF SUMMARY OF THE INVENTION

In a preferred embodiment of the invention, a transesophageal probe with variable stiffness includes an endoscope with a probe head connected to a distal end of the endoscope. A flexible tube is secured to the endoscope and has a semi-rigid rod slidably disposed within the flexible tube.

In an alternative embodiment of the invention, a transesophageal probe with variable stiffness includes an endoscope having an articulation section. The endoscope has a probe head connected to its distal end. A flexible tube is secured within the interior of the endoscope. A semi-rigid rod is slidably disposed within the flexible tube.

The preferred embodiment has a number of advantages. In particular, the semi-rigid rod can be advanced or retracted by an operator to vary the stiffness of the endoscope. This configuration permits the operator to vary the stiffness of the endoscope in order to better accommodate variations in anatomy, particularly esophageal anatomy. Use of different structure for the flexible tube (e.g., a helical structure) or different materials for the semi-rigid rod (e.g., metal) permit additional variations in the stiffness characteristics of the transesophageal probe. Other features and advantages of the invention will become apparent from the description that follows.

BRIEF DESCRIPTION OF THE DRAWINGS

Additional objects and features of the invention will appear from the following description in which the preferred embodiments are set forth in conjunction with the accompanying drawings.

DETAILED DESCRIPTION OF THE INVENTION

Figure 1:
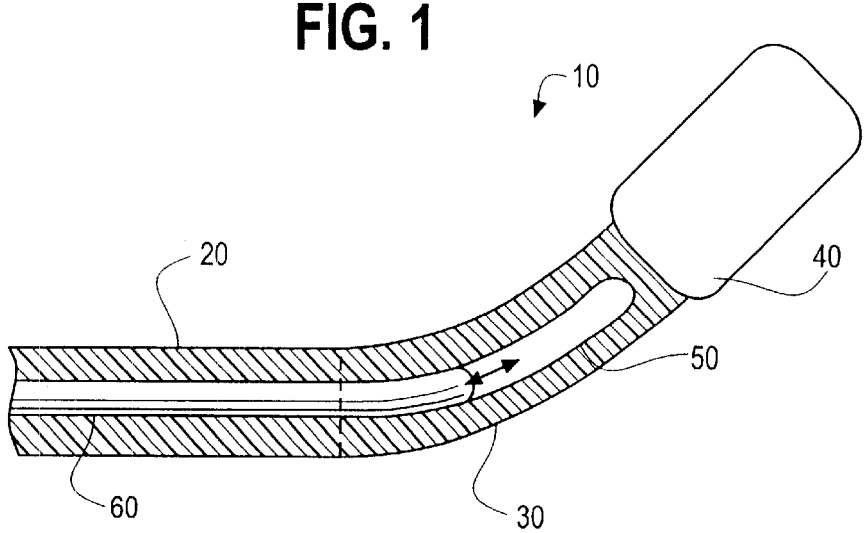
FIG. 1 is a cross-section of the distal portion of one embodiment of transesophageal probe with variable stiffness.

Turning to FIG. 1, one embodiment of the transesophageal probe with variable stiffness 10 is illustrated. The transesophageal probe with variable stiffness 10 includes an endoscope 20 having an articulation section 30. A probe head 40, comprising an ultrasonic transducer for imaging, is attached to the distal end of the articulation section 30 of the endoscope 20. A flexible tube 50 is secured to and disposed within the transesophageal probe with variable stiffness 10. The flexible tube 50 extends from the proximal end of the endoscope 20 to the distal end of the articulation section 30 of the endoscope 20. A semi-rigid rod 60 is slidingly positioned within the flexible tube 50.

In a preferred embodiment, the flexible tube 50 is centered within the endoscope 20 and extends from the proximal end of the endoscope 20 to the distal end of the articulation section 30 of the endoscope 20. The flexible tube 50 may be secured to the interior of the endoscope in any number of ways known to those skilled in the art. The precise means of attachment is not important to the present invention so long as the flexibility of the transesophageal probe with variable stiffness 10 is maintained. Further, the flexible tube 50 may be constructed of any one of a wide variety of conventional plastic materials generally known in the art and may be, for example, tubular, helical, or a mesh, depending on the desired flexibility characteristics.

In one embodiment, the semi-rigid rod 60 slidingly disposed within the flexible tube 50 is made of relatively stiff plastic and is circular in cross-section. The semi-rigid rod 60 is sufficiently long to traverse the entire length of the endoscope 20 and its articulation section 30. The semi-rigid rod 60 may be manually advanced or retracted, at the proximal end of the transesophageal probe 10, into the flexible tube 50. The flexibility of the transesophageal probe 10 can thereby be varied readily, depending on the extent to which the semi-rigid rod 60 is advanced or retracted within the flexible tube 50. In alternative embodiments, the semi-rigid rod 60 may be advanced or retracted, for example, mechanically or electro-mechanically.

Figure 2:
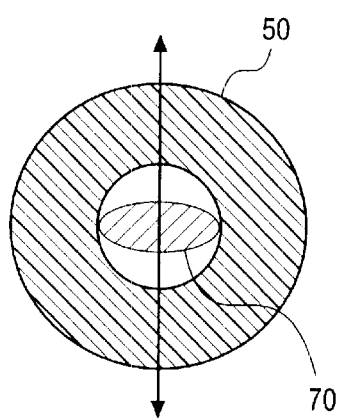
FIG. 2 is a cross-section of an alternative embodiment of a transesophageal probe with variable stiffness using a non-symmetric rod to achieve low transverse stiffness.

Turning to FIG. 2, an alternative embodiment of the transesophageal probe with variable stiffness 10 is illustrated. As before, the semi-rigid rod 60 is slidingly disposed within the flexible tube 50. In this embodiment, however, the semi-rigid rod 60 is a longitudinally non-symmetric rod 70. Use of the longitudinally non-symmetric rod 70 creates low stiffness in the transverse axial direction of the transesophageal probe 10, as illustrated in FIG. 2.

Figure 3:
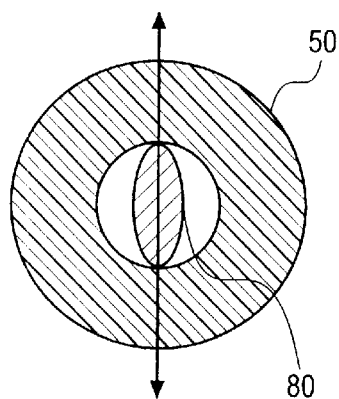
FIG. 3 is a cross-section of an alternative embodiment of a transesophageal probe with variable stiffness using a non-symmetric rod to achieve high transverse stiffness.

Turning to FIG. 3, an alternative embodiment of the transesophageal probe with variable stiffness 10 is illustrated. As before, the semi-rigid rod 60 is slidingly disposed within the flexible tube 50. In this embodiment, however, the semi-rigid rod 60 is a transversely non-symmetric rod 80. Use of the transversely non-symmetric rod 80 creates high stiffness in the transverse axial direction of the transesophageal probe 10, as illustrated in FIG. 3. Therefore, the advancement and rotation of a non-symmetrical rod (e.g., longitudinally non-symmetric rod 70 or transversely non-symmetric rod 80) provide further variable stiffness options to the physician.

In another embodiment, the semi-rigid rod 60 can be helical, tapered, metallic, or of a composite nature. By varying the structure or material composition of the semi-rigid rod 60, the flexibility of the transesophageal probe 10 can be varied in a known manner by advancing or retracting the semi-rigid rod 60.

The present invention thereby provides a transesophageal probe 10 with variable stiffness characteristics. The variable stiffness is achieved by slidably advancing or retracting a semi-rigid rod 60 within a flexible tube 50 disposed within the transesophageal probe 10. Prior limitations on the flexibility of a TEE probe are, thus, eliminated.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A transesophageal probe with variable stiffness comprising:
   an endoscope;
   a probe head connected to a distal end of the endoscope;
   a flexible tube secured entirely within the outer surface of the endoscope; and
   a semi-rigid rod slidably disposed within the flexible tube.

2. The transesophageal probe with variable stiffness of claim 1 wherein the flexible tube is centered within the interior of the endoscope.

3. The transesophageal probe with variable stiffness of claim 1 wherein the endoscope includes an articulation section.

4. The transesophageal probe with variable stiffness of claim 1 wherein the probe head is an ultrasonic transducer.

5. The transesophageal probe with variable stiffness of claim 1 wherein the flexible tube is a helical tube.

6. The transesophageal probe with variable stiffness of claim 1 wherein the flexible tube extends from the proximal end of the endoscope to the distal end of the endoscope.

7. The transesophageal probe with variable stiffness of claim 1 wherein the flexible tube is plastic.

8. A transesophageal probe with variable stiffness comprising:
   an endoscope having an articulation section;
   a probe head connected to a distal end to the endoscope;
   a flexible tube secured entirely within the outer surface of the endoscope; and
   a semi-rigid rod slidably disposed within the flexible tube.

9. The transesophageal probe with variable stiffness of claim 8 wherein the flexible tube is centered within the interior of the endoscope.

10. The transesophageal probe with variable stiffness of claim 8 wherein the probe head is an ultrasonic transducer.

11. The transesophageal probe with variable stiffness of claim 8 wherein the flexible tube is a helical tube.

12. The transesophageal probe with variable stiffness of claim 8 wherein the flexible tube is plastic.

13. The transesophageal probe with variable stiffness of claim 8 wherein the flexible tube extends from the proximal end of the endoscope to the distal end of the articulation section of the endoscope.

14. The transesophageal probe with variable stiffness of claim 8 wherein the semi-rigid rod is plastic.

15. A method of using a transesophageal probe with variable stiffness comprising the steps of:
   inserting into a patient an endoscope having a probe head connected to a distal end of the endoscope and having a flexible tube secured entirely within the outer surface of the endoscope; and
   advancing a semi-rigid rod within the flexible tube to make the endoscope more stiff.

16. The method of claim 15 further comprising the step of retracting the semi-rigid rod within the flexible tube to make the endoscope more flexible.

17. The method of claim 15 further comprising the step of using the probe head to image internal organs using an ultrasonic transducer.

18. The method of claim 15 wherein the endoscope is inserted through a patient's esophagus.

* * * * *